United States Patent [19]
Cheng et al.

[11] Patent Number: 6,066,505
[45] Date of Patent: May 23, 2000

[54] FLUORESCENCE POLARIZATION IMMUNOASSAY

[75] Inventors: Charles Cheng, Bridgewater, N.J.; Raymond Thomas Wong, Brooklyn, N.Y.; Kathryn Sarah Schwenzer, Yardley, Pa.

[73] Assignee: Roche Diagnostics Corporation, Indianapolis, Ind.

[21] Appl. No.: 09/082,823

[22] Filed: May 21, 1998

Related U.S. Application Data

[60] Provisional application No. 60/047,455, May 22, 1997.

[51] Int. Cl.[7] ........................ G01N 33/542; G01N 33/533
[52] U.S. Cl. .......................... 436/537; 436/546; 436/815; 436/816; 436/825
[58] Field of Search ..................................... 436/537, 546, 436/815, 816, 825

[56] References Cited

U.S. PATENT DOCUMENTS

| | | | |
|---|---|---|---|
| 4,252,783 | 2/1981 | Kam et al. | 424/8 |
| 4,492,762 | 1/1985 | Wang et al. | 436/537 |

OTHER PUBLICATIONS

The Merck Index of Chemicals and Drugs, Seventh Edition. Merck & Co., Inc. NJ, USA, p. 791, 1960.

Dandliker, W. B. and Feigen, G. A., *Quantification of the Antigen–Antibody Reaction by the Polarization of Fluorescence*, 1961, vol. 5, No. 4, 299–304.

*Primary Examiner*—Mary E. Ceperley
*Attorney, Agent, or Firm*—Marilyn L. Amink; Roche Diagnostics Corporation

[57] ABSTRACT

In a fluorescence polarization assay for determining the amount of a target analyte in a test sample, wherein the amount of analyte is related to the amount of fluorescence emitted from the analyte-containing reagent medium, the improvement comprising contacting the analyte-containing reagent medium with of at least one compound from the group consisting of 1,10-phenanthroline, 8-hydroxy-7-iodo-5-quinoline, naphthalene-1-sulfonic acid, salts thereof, and any combination thereof.

17 Claims, 1 Drawing Sheet

FLUORESCENCE POLARIZATION IMMUNOASSAY

This application claims priority under 35 U.S.C. § 119(e) of provisional application Ser. No. 60/047,455, filed May 22, 1997.

BRIEF SUMMARY OF THE INVENTION

The invention relates to a method for reducing background fluorescence intensity or endogenous fluorescence, and therefore interference, and improving analyte recovery, in fluorescence polarization immunoassays. One cause of background fluorescence intensity is the presence of bilirubin, primarily bound, in a test sample, for example a clinical sample, being analyzed to quantitate the concentration of a particular target analyte in the sample, for example, a physiologically active substance or compound (e.g., a therapeutic drug). It has now been discovered that when one or more compounds from the group comprising 1,10-phenanthroline, 8-hydroxy-7-iodo-5-quinolinesulfonic acid and naphthalene-1-sulfonic acid, and salts thereof (hereinafter also referred to as "Additives") are added to the sample, a reagent mixture or a reagent mixture containing target in a fluorescence polarization immunoassay, the background intensity or fluorescence is effectively reduced. In addition, recovery of analyte is improved. The reduction in background fluorescence and improvement in recovery increases the accuracy of the results obtained in fluorescence polarization assays. Moreover, the method of the invention does not otherwise adversely affect the performance of the fluorescence polarization assay.

FIGURES

FIG. 1 is a bar graph depicting the ability of the Additives to reduce serum background fluorescence.

BACKGROUND OF THE INVENTION

A fluorescence polarization immunoassay (FPIA) employs a custom-made fluorescent dye, for example, fluorescein-tagged analyte (referred to as a tracer or fluorescein conjugate) to compete in a homogeneous assay system with unlabeled analyte in a sample, for binding to a specific antibody, The principle of the fluorescence polarization immunoassay was first described by W. B. Dandliker and G. A. Feigen, "Quantification of the Antigen-Antibody Reaction by the Polarization of Fluorescence", Biochem. Biophys. Res. Comm. 5:299 (1961). The assay relies on the principle that when a small molecule of fluorescein-tagged analyte is not bound, it rotates freely, but when the fluorescein-tagged analyte is bound to a large antibody molecule, the free rotation is greatly restricted. The degree of tracer rotation is inversely indicated by the fluorescence polarization value which is a calculated value from the measured horizontal and vertical fluorescence intensity of the bound and free fluorescein-tagged analyte in solution. The fluorescence polarization value (mP) is determined by using the measured polarized fluorescence intensities in the following equation:

$$mP = \frac{((T_h - B_h) - (T_v - B_v))}{((T_h - B_h) + (T_v - B_v))}$$

-continued $T_h$: Horizontal test intensity
$T_v$: Veretical test intensity
$B_h$: Horizontal background intensity
$B_v$: Vertical background intensity A standard curve is first established using the fluorescence polarization value of the calibrators, as described hereinafter. When the fluorescence polarization value of the sample is read against the standard curve, the analyte concentration can be determined.

Fluorescein labels are well known in the art and include, for example, 5-[(4,6-dichlorotriazin-2-yl-amino] fluorescein and fluorescein isothiocyanate.

It is desirable to minimize background fluorescence in the assay as much as possible to achieve greater analytical accuracy. It is noted that, in an attempt to increase accuracy, the test intensity is also corrected with the background intensity in the calculation of the fluorescence polarization value. However, the background intensity may not always remain constant during the measurement period. When the background intensity is relatively low compared to the intensity of the tracer, the fluorescence polarization value may not be affected by an inconsistent background intensity value. However, when the initial background intensity, that is, the $B_h$ and $B_v$ intensity values in the formula above, are high and/or unstable or changing, this leads to inconsistencies in the final calculation. More specifically, the inconsistencies may significantly influence the final calculation of polarization (mP) due to the fact that the initial background intensity value, that is, $B_h$ and $B_v$ which is used for the final calculation, may differ from the final or actual background intensity at the time when the total test intensity, that is, $T_h$ and $T_v$ is measured. The test intensity consists of the horizontal and vertical components of the actual background intensity and tracer intensity at the time a sample measurement is made.

In a fluorescence polarization immunoassay, a light source with a wavelength in the range of 475–495 nm is typically used to excite the reaction mixture. A fluorescein-tagged analyte, upon absorbing the light, emits light in less than 10 nanoseconds at a wavelength in the range of 505–530 nm.

Serum, plasma or urine may themselves emit light at a wavelength in the range of 510–520 nm and therefore interfere with the fluorescence polarization measurement. Interference may not be just limited to the presence of bilirubin in the samples. Samples which have low bilirubin level may contain other endogenous or exogenous compounds which generate a very high fluorescence background intensity/or emit light in the range of 510–520 nm. Such samples may generate high background intensity or unstable background intensity and render results obtained from fluorescence polarization assays unreliable for diagnostic or analytical uses. Thus, reduction and/or stabilization of background intensity in a fluorescence polarization immunoassay is required for reliable clinical diagnostic or analytical uses.

DETAILED DESCRIPTION OF THE INVENTION

Figure 1:
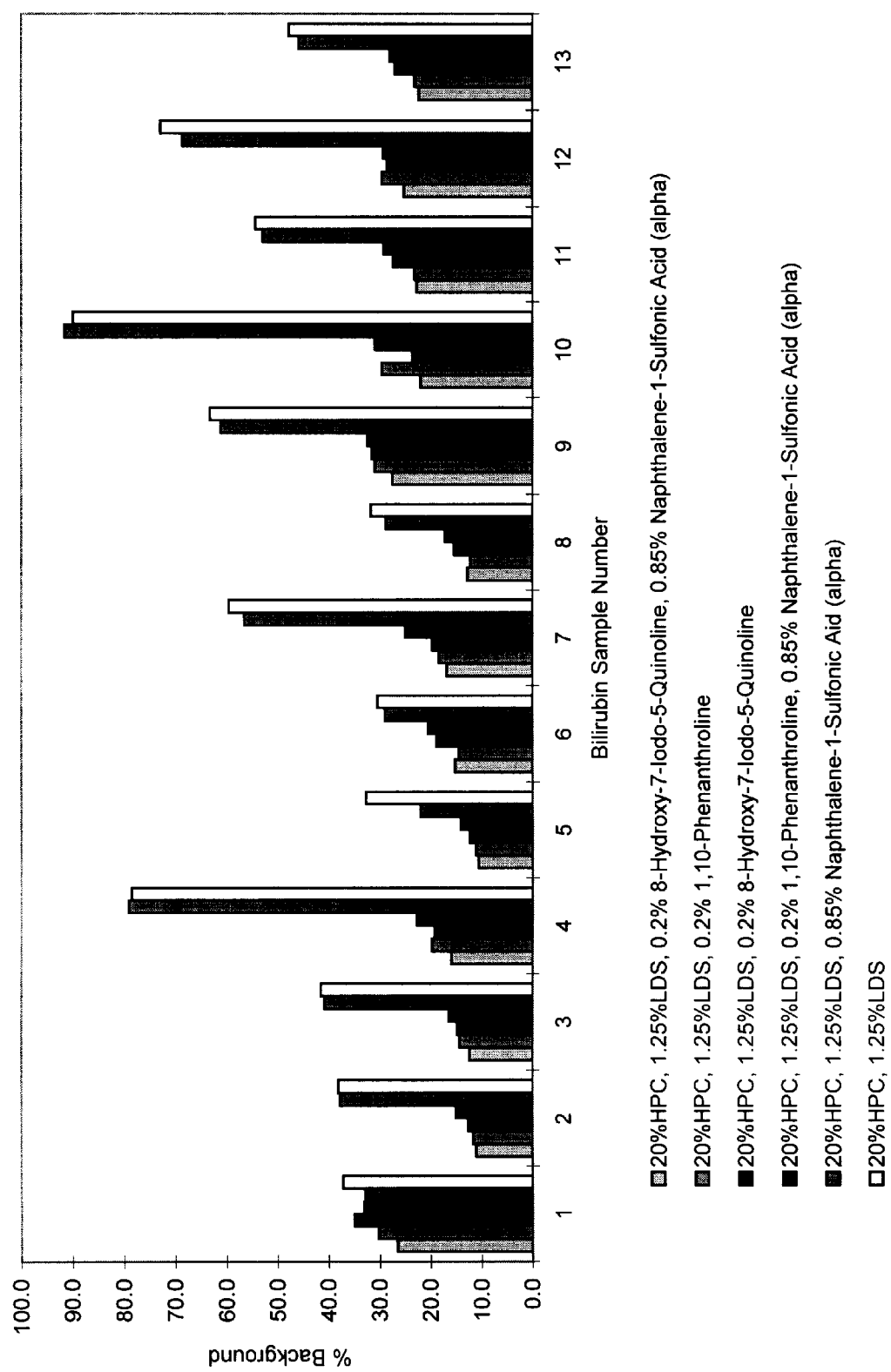

The influence of various additives on background intensity and analyte recovery has been considered in immunoassays, including those with elevated or unstable fluorescence background, in an effort to obtain an immunoassay which can yield an acceptable result for all clinical samples, such as for example, serum, plasma, or urine samples. See U.S. Pat. Nos. 4,252,783 (Kam et al.) and 4,492,762 (Wang et al.).

In accordance with the invention, it has now been discovered that when at least one of the compounds selected from the group consisting of 1,10-phenanthroline, 8-hydroxy-7-iodo-5-quinolinesulfonic acid, naphthalene 1-sulfonic acid, or salts thereof, or a combination of these compounds, is incorporated into the reaction mixture containing an analyte, such as, a barbiturate or a benzodiazepine, in a fluorescence polarization assay, utilizing, for example, the COBAS®INTEGRA analyzer (Roche Diagnostic Systems, Inc., Branchburg, N.J.), the accuracy of such tests is substantially increased. More particularly, the use of 1,10-phenanthroline (Aldrich, St. Louis, Mo.), 8-hydroxy-7-iodo-5-quinolinesulfonic acid (Aldrich, St. Louis, Mo.) or a salt thereof, reduces and stabilizes background intensity in clinical samples which include serum, plasma and urine samples, and generates a reliable mP value. It has also been found that the use of naphthalene-1-sulfonic acid (Fluka, Ronkonkoma, N.Y.), or a salt thereof, improves the analyte recovery.

As used herein "recovery" of an analyte means an accurate measurement of the true value of analyte, in a sample to which has "been added" a known amount of the analyte, that is, the sample is "spiked" with the analyte. "Recovery" of analyte is a significant parameter in assessing the overall accuracy of a fluorescence polarization assay. Thus, 100% "recovery" means that the assay gave the exact value of the true amount of analyte in the sample. A value below 100% means that the assay is under-reporting the amount of analyte actually in the sample. Analogously, a value over 100% indicates that the assay is over-reporting the amount of analyte in the sample.

The compounds 1,10-phenanthroline, 8-hydroxy-7-iodo-5quinolinesulfonic acid and naphthalene-1-sulfonic acid form their corresponding conventional salts, for example, naphthalene-1-sulfonic acid forms, for example, a lithium or sodium salt.

A typical assay is carried out as follows:

A reagent mixture, in accordance with the invention, utilized in a fluorescence polarization immunoassays, typically comprises components A, B, C and D described below.

Component A) Sample

Serum, plasma or urine to be tested for the presence of compounds (analytes), such as, barbiturates or benzodiazepines.

Component B) Diluent

Lithium dodecyl sulfate in the range of from about 0.5% to about 2%; naphthalene-1-sulfonic acid in the range of from about 0.75% to about 5% or more (recovery enhancer); 1,10-phenanthroline in the range from about 0.06% to about 0.25% (background fluorescence reducing agent); hydroxypropyl beta cyclodextrin in the range of from about 10% to about 30%; 8-hydroxy-7-iodo-5-quinolinesulfonic acid (background fluorescence reducing agent) in the range of from about 0.06% to about 0.25%; and alkali metal azide such as, for example, sodium azide, in the range of from about 0.09% to about 3.0%.

Component C) Antibody reagent

Serum barbiturate sheep antisera or serum benzodiazepine sheep antisera. Antisera are raised in sheep by conventional methods well known to one skilled in the art.

Component D) Tracer reagent

Fluorescein-labeled barbiturate or fluorescein-labeled benzodiazepine in a suitable buffer.

Instrument

COBAS®INTEGRA (Roche Diagnostic Systems, Inc., Branchburg, N.J.) or any suitable analyzer to carry out a fluorescence polarization immunoassay.

Protocol For Performing Assay

Antibody reagent, diluent and a sample of blood serum, plasma or urine are added sequentially into a cuvette. After mixing and incubating for a short time (132 seconds on the COBAS®INTEGRA), the background intensity is measured. This is followed by the addition of tracer, incubation of the resulting mixture for a certain time (which, in the COBAS®INTEGRA, is typically 90 seconds) and measurement of the final test intensity.

Determination of a Standard Curve

A standard curve is prepared utilizing standard concentrations of analyte (as hereinafter described in Examples 5 and 6) for the purpose of determining analyte content by reference to the standard curve.

The examples which follow further describe the invention, but are not intended to limit the invention.

EXAMPLE 1

Reduction of Serum Fluorescence in Icteric Serum Samples using Additives of the Invention Sample:

Clinical icteric serum samples.
Diluents:

| | |
|---|---|
| Diluent 1 - Control: | 20% Hydroxypropyl-β-cyclodextrin (HPC), 1.25% lithium dodecyl sulfate (LDS). |
| Diluent 2: | Control plus 0.2% 1,10-phenanthroline, 0.85% naphthalene-1-sulfonic acid (alpha). |
| Diluent 3: | Control plus 0.2% 8-hydroxy-7-iodo-5-quinolinesulfonic acid. |
| Diluent 4: | Control plus 0.2% 1,10-phenanthroline. |
| Diluent 5: | Control plus 0.2% 8-hydroxy-7-ido-5-quinolineuslfonic acid, 0.85% naphthalene-1-sulfonic acid (alpha). |

Antibody reagent

Polyclonal antibody which was raised against nordiazepam in accordance to known procedures. In examples 1–3, the antibody is that currently included in Roche Diagnostic Systems' ONLINE® Benzodiazepine assay.

Tracer reagent

Fluorescein-labeled nordiazepam.

Instrument

COBAS®INTEGRA

Protocol

90 μL antibody reagent, 45 μL sample diluent, and 14 μL sample was added sequentially into a cuvette. After mixing and incubating for a short period of time (typically about 132 seconds), the background intensity of the resulting mixture was measured. This was followed by the addition of 20 μL tracer, incubation of the mixture for a short period of time (again typically about 90 seconds), and measurement of the final test intensity. The resulting measurements are reported below in Table 1.

TABLE 1

| Icteric Sample Number | Bilirubin Conc. (mg/dL) | Background intensity/Test intensity (in %) | | | | |
|---|---|---|---|---|---|---|
| | | Diluent 1 | Diluent 2 | Diluent 3 | Diluent 4 | Diluent 5 |
| 1 | 9.7 | 37 | 33 | 35 | 30 | 27 |
| 2 | * | 38 | 15 | 13 | 12 | 11 |
| 3 | 3.3 | 42 | 17 | 15 | 14 | 12 |
| 4 | 3.5 | 79 | 23 | 19 | 20 | 16 |
| 5 | 5.2 | 33 | 14 | 12 | 11 | 11 |
| 6 | 4.2 | 31 | 21 | 19 | 15 | 15 |
| 7 | 6.0 | 60 | 25 | 20 | 18 | 17 |
| 8 | 6.5 | 32 | 17 | 15 | 12 | 13 |
| 9 | 7.9 | 63 | 32 | 32 | 31 | 28 |
| 10 | 5.4 | 90 | 31 | 24 | 30 | 22 |
| 11 | 7.3 | 54 | 29 | 27 | 23 | 23 |
| 12 | 8.0 | 73 | 29 | 29 | 30 | 25 |
| 13 | 4.7 | 48 | 28 | 27 | 23 | 22 |

*Not tested

Summary of Results

As is demonstrated above in Table 1, diluent 2 is very effective in reducing background fluorescence. This is evidenced by the reduction in Background Intensity/Test Intensity in comparison to diluent 1 (the control).

Similarly, diluent 3, which comprises control with the addition of 8-hydroxy-7-iodo-5-quinolinesulfonic acid, is also very effective in the reducing of serum fluorescence in comparison to diluent 1, and it is even more effective when combined with naphthalenes-1-sulfonic acid (sample diluent 5).

Diluent 4, which comprises control with the addition of 1,10-phenanthroline, is also very effective in reducing background fluorescence, as is evidenced by the reduction in Background Intensity/Test Intensity also in comparison to diluent 1.

The results reported in Table 1 are also summarized in graph form in FIG. 1 with the caveat that FIG. 1 includes one additional diluent, control plus 0.85% naphthalene-1-sulfonic acid, which is not reported in Table 1.

EXAMPLE 2

Recovery of Nordiazepam from Clinical Icteric Samples after the Addition of 1,10-phenanthroline Sample Clinical icteric serum samples were spiked to 70 ng/ml nordiazepam using a stock of 7 $\mu$g/ml.

Diluent

1% Lithium dodecyl sulfate, 15% hydroxypropyl-$\beta$-cyclodextrin with or without 0.15% 1,10-phenanthroline (PAE).

Antibody reagent

Polyclonal antibody raised against nordiazepam.

Tracer reagent

Fuorescein-labeled nordiazepam.

Instrument

COBAS®INTEGRA.

Protocol

95 $\mu$L antibody reagent, 57 $\mu$L sample diluent, and 18 $\mu$L sample were added sequentially into a cuvette. After mixing and incubating for a short period of time, the background intensity was measured. This was followed by the addition of 20 $\mu$L tracer, incubation of the mixture for a short period of time, and the measurement of the final test intensity. The resulting measurements are reported in Table 2.

TABLE 2

The Effect of 1,10-Phenanthroline on Fluorescence Background and Analyte (Nordiazepam) Recovery in Serum.

| 1 Icteric Sample ID | 2 Total Bilirubin mg/dL | 3 Recovery Analyte ng/mL without | 4 Recovery Analyte ng/mL with | 5 Recovery Analyte (%) without | 6 Recovery Analyte (%) with | 7 Background/Test Intensity (%) without | 8 Background/Test Intensity (%) with | 9 Reduction in Background (%)* |
|---|---|---|---|---|---|---|---|---|
| Control | 0 | 73.37 | 68.85 | | | | | |
| 1 | 2.1 | 74.43 | 57.41 | 101% | 83% | 37 | 8 | 78% |
| 2 | 5.3 | 91.48 | 71.4 | 125% | 104% | 57 | 22 | 61% |
| 3 | 5.3 | 92.74 | 69.55 | 126% | 101% | 42 | 19 | 55% |
| 4 | 5.6 | 97.36 | 69.05 | 133% | 99% | 52 | 19 | 63% |
| 5 | 5.8 | 81.77 | 65.4 | 111% | 95% | 28 | 17 | 39% |
| 6 | 7.2 | 103.09 | 64.88 | 141% | 87% | 57 | 30 | 47% |
| 7 | 7.3 | 32.98 | 99.09 | 45% | 144% | 60 | 36 | 40% |
| 8 | 10.5 | 85.58 | 74.66 | 117% | 108% | 35 | 27 | 23% |
| 9 | 14.1 | 71.08 | 67.39 | 97% | 98% | 38 | 32 | 16% |
| 10 | 26.1 | 45.08 | 42.91 | 61% | 62% | 53 | 48 | 9% |
| 11 | 44.4 | 36.03 | 26.66 | 49% | 39% | 55 | 53 | 4% |

*% Reduction in background (Column 9) = $\dfrac{(\text{Column 7} - \text{Column 8})\,100}{\text{Column 7}}$ Summary of Results As is shown in Table 2, the use of 18 $\mu$L of icteric serum sample generated a high background intensity of up to 60% of the final tracer signal (see column 7). The background intensities of these high background intensity samples were significantly suppressed (reduced), up to 78% reduction, with the addition of 1,10-phenanthroline (see column 9). However, samples with background intensities greater than 32% even with the addition of 1,10-phenanthroline (see column 8, e.g. last three entries), gave results for recovery of nordiazepam in serum which were unacceptably low for a diagnostic assay. This means, referring to column 6, the last two entries, the measured amount of analyte was significantly below 100%. Analogously, certain samples (see again column 6), yielded an over-recovery of spiked analyte (above 100% recovery). It is also noted that while there was a reduction in background fluorescence, satisfactory analytical recovery of analyte could not be achieved in these samples merely with use of 1,10-phenathroline.

EXAMPLE 3

Accurate Recovery of Nordiazepam from Icteric Serum Samples after the Addition of Naphthalene-1-Sulfonic acid Sample Clinical icteric samples were spiked to 150 ng/mL of nordiazepam using a stock of 15 µg/mL.

Diluent 1.25% Lithium dodecyl sulfate, 20% hydroxypropyl-β-cyclodextrin, 0.2% 1,10-phenanthroline with and without 0.85% naphthalene-1-sulfonic acid.

Antibody reagent

Polyclonal antibody raised against nordiazepam.

Tracer reagent

Fluorescein-labeled nordiazepam.

Instrument

COBAS®INTEGRA (Roche Diagnostic Systems, Inc., Branchburg, N.J.).

Protocol without naphthalene-1-sulfonic acid

95 µL antibody reagent, 45 µL sample diluent without naphthalene-1-sulfonic acid, and 14 µL sample were added sequentially to a cuvette. After mixing and incubating for a short period of time, the background intensity was measured. This was followed by the addition of 20 µL tracer, incubation of the mixture for a short period of time, and the measurement of the final test intensity.

Protocol with 0.85% naphthalene-1-sulfonic acid

90 µL antibody reagent, 45 µL sample diluent containing 0.85% napthalene-1-sulfonic acid and 14 µL sample were added sequentially to a cuvette. After mixing and incubating for a short period of time, the background intensity was measured. This was followed by the addition of 20 µL tracer, incubation of the mixture for a short period of time, and the measurement of the final test intensity.

The results of these measurements are provided below in Table 3.

TABLE 3

| 1 | 2 | 3 | 4 | 5 |
|---|---|---|---|---|
| Bilirubin Conc. | Nordiazepam Recovered (ng/mL) | | Nordiazepam Recovered (%) | |
| (mg/dL) | Without | With | Without | With |
| 0 | 132 | 129 | — | — |
| 5 | 166 | 138 | 126 | 106 |
| 10 | 181 | 141 | 137 | 109 |
| 20 | * | 139 | * | 107 |

*Invalid result due to high background.

Table 3 depicts the problem of "over-recover" of analyte in normal human serum which was spiked with bilirubin. The bilirubin interferes with the measurement and yields a test result which is higher than the true content of the analyte in the sample. Thus, in column 4, the resulting analyte value obtained without added napthalene-1-sulfonic to acid is substantially higher than the known true value of 100%. In contrast, upon addition of naphthalene-1-sulfonic acid, the resulting measurement is decidedly closer to the known true value of 100% (See column 5).

EXAMPLE 4

Accurate Recovery of Secobarbital from Icteric Serum Samples after the Addition of Naphthalene-1-Sulfonic Acid Sample Clinical icteric samples were spiked to 1000 ng/mL of secobarbital using a stock of 100 µg/mL.

Sample diluent 1.25% Lithium dodecyl sulfate, 20% hydroxypropyl-β-cyclodextrin, 0.2% 1,10-phenanthroline with and without 0.85% naphthalene-1-sulfonic acid.

Antibody reagent

Polyclonal antibody which was raised against secobarbital in accordance to known procedures. In examples 4 and 5, the antibody is that currently used in Roche Diagnostic Systems' ONLINE® Secobarbital assay.

Tracer reagent

Fluorescein-labeled secobarbital.

Instrument

COBAS®INTEGRA

Protocol without naphthalene-1-sulfonic acid

95 µL antibody reagent, 45 µL sample diluent without naphthalene-1-sulfonic acid, and 4 µL sample were added sequentially to a cuvette. After mixing and incubating for a short period of time, the background intensity was measured. This was followed by the addition of 20 µL tracer, incubation of the mixture for a short period of time and the measurement of the final test intensity.

Protocol with 0.85% naphthalene-1-sulfonic acid

90 µL antibody reagent, 45 µL sample diluent containing 0.85% naphthalene-1-sulfonic acid, and 4 µL sample were added sequentially into a cuvette. After mixing and incubating for a short period of time, the background intensity was measured. This was followed by the addition of 20 µL tracer, incubation of the mixture for a short period of time and the measurement of the final test intensity.

The results of these measurements are provided below in Table 4.

TABLE 4

| 1 | 2 | 3 | 4 | 5 |
|---|---|---|---|---|
| Bilirubin Conc. | Secobarbital Recovered (ng/mL) | | Secobarbital Recovered (%) | |
| (mg/dL) | Without | With | Without | With |
| 0 | 960 | 991 | — | — |
| 5 | 955 | 1038 | 99 | 104 |
| 10 | 1130 | 1057 | 118 | 106 |
| 20 | 1192 | 1054 | 124 | 106 |

Table 4 also exemplifies the correction of "over-recovery" of analyte in spiked samples through the use of naphthalene-1-sulfonic acid.

EXAMPLE 5

Set (or Assemblage) of Reagents for Serum Barbiturates Assay

Serum Barbiturates Antibody Reagent Component Concentrations pH 7.5, 0.1M: Ingredients 0.1 M Tris buffer, pH 7.5 containing 1% ethylene glycol, 0.056% riboflavin binding protein, 0.09% sodium azide and sheep serum raised against secobarbital at a suitable dilution or titer.

Serum Barbiturates Tracer Reagent Component Concentrations pH 8.0, 0.1 M: Ingredients 0.1 M Phosphate buffer, pH 8, containing 0.01% bovine gamma globulin, 0.09% sodium azide and a tracer which is secobarbital labeled with fluorescein.

Diluent Component Concentration: Ingredients 0.85% naphthalene-1-sulfonic acid, 20% sodium salt of hydroxypropyl beta cyclodextrin, 0.20% 1,10-phenanthroline monohydrate, 1.25% dodecyl sulfate, lithium salt, 0.09% sodium azide.

Serum Barbiturates Calibrators (also referred as Standards)

Calibrators were prepared by spiking secobarbital at 0, 0.5, 1, 2, and 4 μg/mL, respectively, into drug free normal human serum.

Fluorescence polarization was read following incubation. The polarization readings changed and allowed for the construction of a standard curve. Unknown samples were tested in a similar manner and the analyte, e.g. barbiturate, benzodiazepine and the like, content is calculated utilizing the standard curve.

EXAMPLE 6

Set (or assemblage) of Reagents for Serum Benzodiazepines Assay

Serum Benzodiazepines Antibody Reagent Component Concentrations pH 7.5, 01M: Ingredients:

0.1$\underline{M}$ Tris buffer, pH 7.5 containing 1% ethylene glycol, 0.056% riboflavin binding protein, 0.09 % sodium azide and sheep serum raised against benzodiazepine at a suitable dilution or titer.

Serum Benzodiazepines Tracer Reagent Component Concentrations pH 7.0, 0.1 M: Ingredients 0.1 $\underline{M}$ ACES buffer at pH 7.0 containing 1% ethylene glycol, 0.01% bovine gamma globulin, 0.09% sodium azide and a tracer which is nordiazepam labeled with fluorescein.

Diluent Ingredients

85% Naphthalene-1-sulfonic acid (alpha), 20% sodium salt of hydroxypropyl beta cyclodextrin, 0.20% 1,10-phenanthroline monohydrate, 1.25% dodecyl sulfate, lithium salt, 0.09% sodium azide.

Serum Benzodiazepine Calibrators

Calibrators were prepared in normal human serum using nordiazepam at 0, 25, 50, 100 and 200 ng/mL, as previously described for secobarbital.

What is claimed:

1. In a method for quantitating the amount of an analyte, if any, present in a test sample, in a fluorescence polarization immunoassay, the improvement comprising contacting the analyte, either in the clinical sample or a reagent mixture containing said analyte, with at least one compound selected from the group consisting of 1,10-phenanthroline, 8-hydroxy-7-iodo-5-quinolinesulfonic acid, naphthalene-1-sulfonic acid, and salts thereof, and any combination thereof, said compound being in an amount sufficient to reduce background interference from fluorescent substances endogenous to said sample.

2. The method of claim 1, wherein the test sample is a clinical sample selected from serum, plasma or urine.

3. The method of claim 2, wherein the selected compound is 1,10-phenanthroline.

4. The method of claim 2, wherein the selected compound is 8-hydroxy-7-iodo-5-quinolinesulfonic acid.

5. The method of claim 2, wherein the selected compounds in combination are naphthalene-1-sulfonic acid and 1,10-phenanthroline.

6. The method of claim 2, wherein the selected compounds in combination are naphthalene-1-sulfonic acid and 8-hydroxy-7-iodo-5-quinolinesulfonic acid.

7. In a fluorescence polarization immunoassay for a target analyte in a test sample, the improvement comprising reducing background interference by contacting the analyte-containing clinical sample or an analyte-containing reagent mixture with an effective amount of at least one compound selected from the group consisting of 1,10-phenanthroline, 8-hydroxy-7-iodo-5-quinolinesulfonic acid, and salts thereof.

8. A method of reducing interference in a fluorescence polarization immunoassay for a target analyte in a test sample comprising adding to said test sample or to a reagent mixture containing said test sample an effective amount of at least one compound selected from the group consisting of 1,10-phenanthroline, 8-hydroxy-7-iodo-5-quinolinesulfonic acid, naphthalene-1-sulfonic acid, and the salts thereof.

9. The method of claim 8 wherein the test sample is a clinical sample which is selected from serum, plasma or urine.

10. A set of reagents for the performance of a fluorescence polarization immunoassay for the quantitation of an analyte in a test sample, said reagents comprising a fluorescein-tagged analyte and antibody for said analyte, the improvement comprising the inclusion in said reagents of at least one compound selected from the group consisting of 1,10-phenanthroline, 8-hydroxy-7-iodo-5-quinolinesulfonic acid, and salts thereof and, optionally, naphthalene-1-sulfonic acid.

11. The set of reagents of claim 10, wherein the test sample is a clinical sample selected from serum, plasma, or urine.

12. The set of reagents of claim 11, wherein the selected compound is 1,10-phenanthroline.

13. The set of reagents of claim 11, wherein the selected compound is 8-hydroxy-7-iodo-5-quinolinesulfonic acid.

14. A set of reagents for the performance of a fluorescence polarization immunoassay, comprising:

1) lithium dodecyl sulfate in the range from about 0.5% to about 2%;

2) hydroxypropyl beta cyclodextrin in the range from about 10% to about 30%;

3) 1,10-phenanthroline in the range of from about 0.06% to about 0.25%; and 4) alkali metal azide in the range from about 0.09% to about 3.0%.

15. The set of reagents of claim 14 further comprising naphthalene-1-sulfonic acid in the range from about 0.75% to about 5%.

16. The set of reagents of claim 15 wherein the alkali metal azide, item 4), is sodium azide.

17. A reagent for a fluorescence polarization assay, said reagent comprising 0.85% naphthalene-1-sulfonic acid (alpha), 20% sodium salt of hydroxypropyl beta cyclodextrin, 0.20% 1,10-phenanthroline monohydrate, 1.25% dodecyl sulfate, lithium salt, and 0.09% sodium azide.

* * * * *